United States Patent
Mullins et al.

(10) Patent No.: US 9,169,352 B2
(45) Date of Patent: Oct. 27, 2015

(54) AROMATIC DICYANATE COMPOUNDS WITH HIGH ALIPHATIC CARBON CONTENT

(71) Applicant: Dow Global Technologies LLC, Midland, MI (US)

(72) Inventors: Michael J. Mullins, Houston, TX (US); Robert E. Hefner, Jr., Rosharon, TX (US); Ulrich Herold, Bühl (DE); Mark B. Wilson, Clute, TX (US)

(73) Assignee: Blue Cube IP LLC, Midland, MI (US)

( * ) Notice: Subject to any disclaimer, the term of this patent is extended or adjusted under 35 U.S.C. 154(b) by 0 days.

(21) Appl. No.: 14/626,745

(22) Filed: Feb. 19, 2015

(65) Prior Publication Data

US 2015/0166727 A1 Jun. 18, 2015

Related U.S. Application Data

(62) Division of application No. 12/921,440, filed as application No. PCT/US2009/036517 on Mar. 9, 2009, now Pat. No. 9,045,394.

(60) Provisional application No. 61/035,816, filed on Mar. 12, 2008.

(51) Int. Cl.
| C07C 261/00 | (2006.01) |
| C08G 73/00 | (2006.01) |
| C07C 261/02 | (2006.01) |

(52) U.S. Cl.
CPC .............. *C08G 73/00* (2013.01); *C07C 261/02* (2013.01); *C07C 2101/14* (2013.01); *C07C 2101/18* (2013.01); *C07C 2103/38* (2013.01)

(58) Field of Classification Search
None
See application file for complete search history.

(56) References Cited

U.S. PATENT DOCUMENTS

| 3,694,410 | A | 9/1972 | Oehmke et al. |
| 4,094,852 | A | 6/1978 | Sundermann et al. |
| 4,110,364 | A | 8/1978 | Gaku et al. |
| 4,438,241 | A | 3/1984 | Mark et al. |
| 4,554,309 | A | 11/1985 | Mark et al. |
| 4,554,330 | A | 11/1985 | Mark et al. |
| 6,037,438 | A | 3/2000 | Endo et al. |
| 6,121,484 | A | 9/2000 | Falchetto |
| 8,729,181 | B2 | 5/2014 | Mullins et al. |
| 2011/0009560 | A1 | 1/2011 | Hefner, Jr. et al. |
| 2011/0098380 | A1 | 4/2011 | Hearn et al. |

FOREIGN PATENT DOCUMENTS

| EP | 0165361 A1 | 12/1985 |
| EP | 612783 A1 | 8/1994 |
| JP | 7149893 | 6/1995 |
| JP | 2005187335 A | 7/2005 |
| JP | 4282336 B2 | 6/2009 |
| JP | 5148325 B2 | 2/2013 |
| WO | 86/00080 A1 | 1/1986 |

OTHER PUBLICATIONS

Martin and Bauer, Organic Synthesis, Cyanic Acid Esters from Phenols: Phenyl Cyanate, 1983, pp. 35-38, vol. 61, Wiley and Sons.
Korshak V. V. et al, Synthesis and Investigation, of Aryl Dicyanate Copolymers, High Molecular Compounds, 1975, pp. 22-27, vol. 17.
International Search Report and Written Opinion for PCT/US2009/036517, Mail Date Aug. 6, 2009, pp. 1-10.
International Preliminary Report on Patentability, Chapter I of the PCT for PCT/US2009/036517, Mail Date Sep. 14, 2010, pp. 1-7.

*Primary Examiner* — Michael L Leonard

(57) ABSTRACT

Aromatic dicyanate compounds which comprise aliphatic moieties having at least about six carbon atoms and resins and thermoset products based on these compounds.

15 Claims, No Drawings

AROMATIC DICYANATE COMPOUNDS WITH HIGH ALIPHATIC CARBON CONTENT

This Application is a Divisional Application of Ser. No. 12/921,440, filed on Sep. 8, 2010; which is a 371 Application of International Application No. PCT/US09/36517, filed on Mar. 9, 2009; which claims the benefit of U.S. Provisional Application No. 61/035,816, filed on Mar. 12, 2008, and fully incorporated herein by reference.

BACKGROUND OF THE INVENTION

1. Field of the Invention

The present invention relates generally to aromatic dicyanate compounds which comprise aliphatic moieties having at least about six carbon atoms and to resins and thermoset products based on these compounds.

2. Discussion of Background Information

The performance requirements for thermosetting resins used in electrical applications continue to escalate. In particular, high frequency electronics have become more commonplace with advances in computer, communications, and wireless technologies. In view thereof, there is a need for resins which show reduced dielectric constants and dissipation factors as well as enhanced thermal resistance.

Aromatic cyanate compounds have been used in electronics applications for many years. The most common cyanate, bisphenol A dicyanate of the following formula:

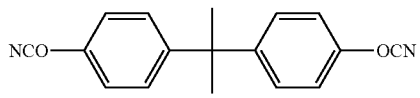

can be prepared by reaction of bisphenol A (isopropylidene diphenol) with a cyanogen halide, for example, cyanogen bromide, in the presence of an acid acceptor, for example, triethylamine. Another known aromatic dicyanate compound is the dicyanate of cyclohexanone bisphenol. See, e.g., EP 612 783, the entire disclosure whereof is expressly incorporated by reference herein.

SUMMARY OF THE INVENTION

It has now been found that the dielectric properties of resins produced from aromatic cyanate compounds can be improved by increasing the hydrocarbon content of the cyanate compound.

Specifically, the present inventors have found, inter alia, a class of aromatic dicyanate compounds which contain a high percentage of non-polar hydrocarbon groups and afford resins with an improved combination of (low) dielectric constants and dissipation factors, along with a high glass transition temperature Tg. While it was speculated that the incorporation of a large hydrocarbon structure would be deleterious to the thermal properties and the cure profile of a thermosettable mixture incorporating these dicyanate compounds, the exact opposite was observed (see Examples below). Thus, the hydrocarbon portion of the aromatic dicyanate compounds was found to be desirable because it affords enhanced thermal resistance, low moisture absorption and excellent dielectric properties, without a deleterious effect on the cure behavior of a thermosettable mixture prepared therefrom or the Tg of cured products made therefrom. It was unexpectedly found that the increased hydrocarbon content of the aromatic dicyanate compounds of the present invention can moderate the enthalpic cure energy without increasing the cure onset and end temperatures. This reduction in exothermicity on cure can help to prevent damage such as cracking or delamination which may result from the cure of dicyanates which comprise a smaller proportion of non-polar hydrocarbon groups than the dicyanates of the present invention.

The present invention provides aromatic dicyanate compounds of formula (I):

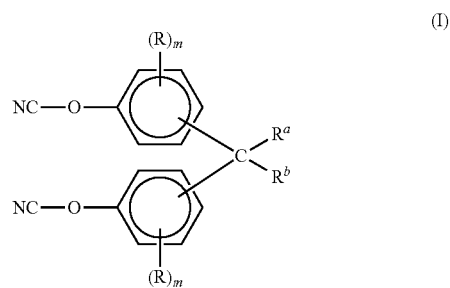

(I)

wherein:
each m independently is 0, 1, or 2;
the moieties $R^a$ and $R^b$ independently represent optionally substituted aliphatic groups having a total of from about 5 to about 24 carbon atoms and $R^a$ and $R^b$ together with the carbon atom to which they are bonded may form an optionally substituted and/or optionally unsaturated and/or optionally polycyclic aliphatic ring structure which has at least about 8 ring carbon atoms; and
the moieties R independently represent halogen, cyano, nitro, optionally substituted alkyl, optionally substituted cycloalkyl, optionally substituted alkoxy, optionally substituted alkenyl, optionally substituted alkenyloxy, optionally substituted aryl having from 6 to about 10 carbon atoms, optionally substituted aralkyl having from 7 to about 12 carbon atoms, optionally substituted aryloxy having from 6 to about 10 carbon atoms, and optionally substituted aralkoxy having from 7 to about 12 carbon atoms.

In one aspect, the aromatic dicyanate compounds of formula (I) may be aromatic dicyanate compounds of formula (Ia):

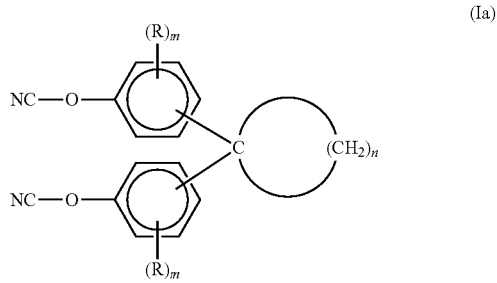

(Ia)

wherein:
n has a value of from about 7 to about 24;
each m independently is 0, 1, or 2; and
the moieties R independently represent halogen, cyano (—CN), nitro, unsubstituted or substituted alkyl preferably having from 1 to about 6 carbon atoms, unsubstituted or substituted cycloalkyl preferably having from about 5 to about 8 carbon atoms, unsubstituted or substituted alkoxy preferably having from 1 to about 6 carbon atoms, unsubstituted or substituted alkenyl preferably having from 3 to about 6 carbon atoms, unsubstituted or substituted alkenyloxy preferably having from 3 to about 6 carbon atoms, unsubstituted or substituted aryl preferably having from 6 to about 10 carbon atoms, unsubstituted or substituted aralkyl preferably having from 7 to about 12 carbon atoms, unsubstituted or substituted aryloxy preferably having from 6 to about 10 carbon atoms, and unsubstituted or substituted aralkoxy preferably having from 7 to about 12 carbon atoms;
and any non-aromatic cyclic moieties comprised in the above formula (Ia) may optionally carry one or more substituents and/or may optionally comprise one or more double bonds and/or may optionally be polycyclic (e.g., bicyclic or tricyclic).

In one aspect of the aromatic dicyanate compounds of formula (Ia), n may have a value of from about 9 to about 16; for example, n may have a value of 9, 10, or 11 and may in particular equal 11.

In one aspect of the compounds of formula (I)/(Ia), each m may independently be 0 or 1.

Non-limiting examples of the dicyanates of formula (I)/(Ia) include 1,1-bis(4-cyanatophenyl)cyclododecane, 1,1-bis(4-cyanato-3,5-dimethylphenyl)cyclododecane, 1,1-bis(4-cyanato-3-methylphenyl)cyclododecane, 1,1-bis(4-cyanatophenyl)cyclodecane, 2,2-bis(4-cyanatophenyl)adamantane, 4,4'-bis(4-cyanatophenyl)octahydro-1,4:5,8-dimethanonaphthalen-2(1H)ylidene and 5,5-bis(4-cyanatophenyl)hexahydro-4,7-methanoindane. A preferred example of the compounds of formula (I)/(Ia) is 1,1-bis(4-cyanatophenyl)cyclododecane.

The present invention also provides polymers (i.e., homo- and copolymers) and prepolymers of the dicyanate compounds of formula (I) set forth above (including the various aspects thereof).

The present invention also provides a first polymerizable mixture which comprises at least one aromatic dicyanate compound of the present invention as set forth above (including the various aspects thereof) and/or a prepolymer thereof and one or more substances which are selected from polymerization catalysts, co-curing agents, flame retardants, synergists for flame retardants, solvents, fillers, adhesion promoters, wetting aids, dispersing aids, surface modifiers, thermoplastic polymers, and mold release agents.

The present invention also provides a second polymerizable mixture which comprises (i) at least one aromatic dicyanate compound of the present invention as set forth above (including the various aspects thereof) and/or a prepolymer thereof and (ii) at least one compound and/or a prepolymer thereof which is capable of reacting with (i).

In one aspect of the second mixture, the at least one compound (ii) may be selected from compounds which comprise one or more polymerizable ethylenically unsaturated moieties, aromatic di- and polycyanates which are different from a dicyanate of formula (I), aromatic di- and polycyanamides, di- and polymaleimides, and di- and polyglycidyl ethers.

In another aspect, the second mixture may further comprise one or more substances which are selected from polymerization catalysts, co-curing agents, flame retardants, synergists for flame retardants, solvents, fillers, adhesion promoters, wetting aids, dispersing aids, surface modifiers, thermoplastic polymers, and mold release agents.

In another aspect, each of the above first and second mixtures may be partially or completely polymerized and the present invention also provides a product which comprises such a polymerized mixture.

In one aspect, the product may comprise at least one of an electrical laminate, an IC (integrated circuit) substrate, a casting, a coating, a die attach and mold compound formulation, a composite, and an adhesive.

The present invention also provides a process for preparing a dicyanate compound of the present invention as set forth above (including the various aspects thereof). The process comprises the reaction a compound of formula (II):

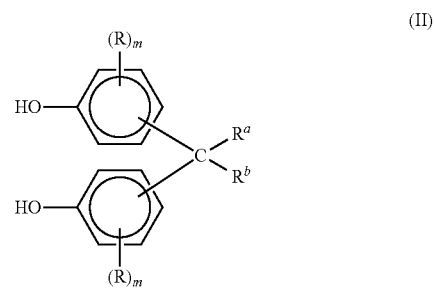

(II)

wherein m, $R^a$, $R^b$ and R are as set forth above with respect to formula (I), in a solvent with an at least about stoichiometric quantity of a cyanogen halide in the presence of an at least about stoichiometric quantity of a base.

In one aspect of the process, the cyanogen halide may comprise cyanogen chloride and/or cyanogen bromide.

In another aspect, the reaction may be carried out at a temperature of from about −40° C. to about 60° C.

In yet another aspect of the process of the present invention, the base may comprise one or more of sodium hydroxide, potassium hydroxide, trimethylamine, and triethylamine and in particular, triethylamine.

In a still further aspect of the process, the solvent may comprise one or more of water, an aliphatic ketone, a chlorinated hydrocarbon, an aliphatic or cycloaliphatic ether or diether, and an aromatic hydrocarbon. For example, the solvent may comprise one or more of acetone, methylethylketone, methylene chloride, and chloroform.

Other features and advantages of the present invention will be set forth in the description of invention that follows, and will be apparent, in part, from the description or may be learned by practice of the invention. The invention will be realized and attained by the compositions, products, and methods particularly pointed out in the written description and claims hereof.

DETAILED DESCRIPTION OF THE PRESENT INVENTION

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show embodiments of the present invention in more detail than is necessary for the fundamental understanding of the present invention, the description making apparent to those skilled in the art how the several forms of the present invention may be embodied in practice.

As set forth above, the present invention provides, inter alia, aromatic dicyanate compounds of formula (I):

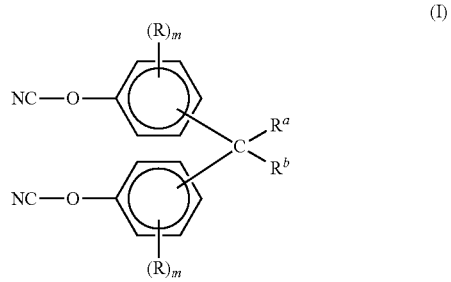

The moieties $R^a$ and $R^b$ in the above formula may independently represent optionally substituted aliphatic groups having a total of from about 5 to about 24 carbon atoms. Usually, the total number of carbon atoms in the aliphatic moieties $R^a$ and $R^b$ will be at least about 6, e.g., at least about 7, at least about 8, at least about 9, or at least about 10, but will usually be not higher than about 18, e.g., not higher than about 16, or not higher than about 14. The aliphatic moieties may be linear, branched or cyclic and saturated or unsaturated. Non-limiting examples thereof are linear or branched alkyl groups and alkenyl groups, cycloalkyl and cycloalkenyl groups as well as alkylcycloalkyl and cycloalkylalkyl groups such as, e.g., methyl, ethyl, n-propyl, isopropyl, n-butyl, n-pentyl, n-hexyl, n-heptyl, n-octyl, n-nonyl, n-decyl, n-undecyl, n-dodecyl, cyclohexyl, methylcyclohexyl, and cyclohexylmethyl, and the corresponding mono- and diunsaturated groups. Further, these groups may be substituted by one or more (e.g., 1, 2, 3, or 4) substituents. Non-limiting examples of substituents are F, Cl and Br as well as aromatic groups (such as, e.g., phenyl). Also, often one of the moieties $R^a$ and $R^b$ will represent methyl or ethyl, in particular, methyl.

The moieties $R^a$ and $R^b$ in the above formula (I) may also form, together with the carbon atom to which they are bonded, an optionally substituted and/or optionally polycyclic aliphatic ring structure which has at least about 8 ring carbon atoms. Examples of corresponding compounds are those of formula (Ia):

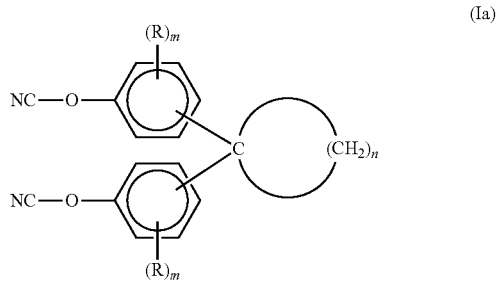

The value of n in the above formula (Ia) is not lower than about 7, e.g., not lower than about 8, not lower than about 9, or not lower than about 10, and not higher than about 24, e.g., not higher than about 16, not higher than about 14, or not higher than about 12, and preferably equals 8, 9, 10, 11, or 12, in particular 11 (i.e., giving rise to a cyclododecylidene structure).

The cycloaliphatic moiety shown in the above formula (Ia) may optionally be polycyclic (e.g., bicyclic or tricyclic) and/or may optionally comprise one or more (e.g., 1, 2, 3, or 4) double bonds and/or may optionally carry one or more (e.g., 1, 2, or 3) substituents. If more than one substituent is present, the substituents may be the same or different. Non-limiting examples of substituents which may be present on the cycloaliphatic moiety include alkyl groups, e.g., optionally substituted alkyl groups having from 1 to about 6 carbon atoms (e.g., methyl or ethyl), and halogen atoms such as, e.g., F, Cl, and Br. The alkyl groups may be substituted with, for example, one or more halogen atoms such as, e.g., F, Cl, and Br.

The value of each m in the above formula (I)/(Ia) independently is 0, 1 or 2. Preferably, the values of m are identical and/or are 0 or 1.

The moieties R in the above formula (I)/(Ia) independently represent halogen (e.g., F, Cl, and Br, preferably Cl or Br), cyano, nitro, unsubstituted or substituted alkyl preferably having from 1 to about 6 carbon atoms, unsubstituted or substituted cycloalkyl preferably having from about 5 to about 8 carbon atoms, unsubstituted or substituted alkoxy preferably having from 1 to about 6 carbon atoms, unsubstituted or substituted alkenyl preferably having from 3 to about 6 carbon atoms, unsubstituted or substituted alkenyloxy preferably having from 3 to about 6 carbon atoms, unsubstituted or substituted aryl preferably having from 6 to about 10 carbon atoms, unsubstituted or substituted aralkyl preferably having from 7 to about 12 carbon atoms, unsubstituted or substituted aryloxy preferably having from 6 to about 10 carbon atoms, and unsubstituted or substituted aralkoxy preferably having from 7 to about 12 carbon atoms.

It is to be appreciated that whenever the terms "alkyl" and "alkenyl" are used in the present specification and the appended claims, these terms also include the corresponding cycloaliphatic groups such as, e.g., cyclopentyl, cyclohexyl, cyclopentenyl, and cyclohexenyl. Also, where two alkyl and/or alkenyl groups are attached to two (preferably adjacent) carbon atoms of an aliphatic or aromatic ring, they may be combined to form an alkylene or alkenylene group which together with the carbon atoms to which this group is attached results in a preferably 5- or 6-membered ring structure. In the case of non-adjacent carbon atoms, this ring structure may give rise to a bicyclic compound.

The above alkyl groups and alkoxy groups R will often comprise from 1 to about 4 carbon atoms and in particular, 1 or 2 carbon atoms. Non-limiting specific examples of these groups include, methyl, ethyl, propyl, isopropyl, n-butyl, isobutyl, sec-butyl and tert-butyl and methoxy, ethoxy, propoxy, isopropoxy, n-butoxy, isobutoxy, sec-butoxy, and tert-butoxy. The alkyl and alkoxy groups may be substituted with one or more (e.g., 1, 2, or 3) substituents. If more than one substituent is present, the substituents may be the same or different and are preferably identical. Non-limiting examples of these substituents include halogen atoms such as, e.g., F, Cl, and Br. Non-limiting specific examples of substituted alkyl and alkoxy groups include $CF_3$, $CF_3CH_2$, $CCl_3$, $CCl_3CH_2$, $CHCl_2$, $CH_2Cl$, $CH_2Br$, $CCl_3O$, $CHCl_2O$, $CH_2ClO$, and $CH_2BrO$.

The above alkenyl and alkenyloxy groups will often comprise 3 or 4 carbon atoms and in particular, 3 carbon atoms. Non-limiting specific examples of these groups are allyl, methallyl, and 1-propenyl. The alkenyl and alkenyloxy groups may be substituted with one or more (e.g., 1, 2, or 3) substituents. If more than one substituent is present, the substituents may be the same or different and are preferably identical. Non-limiting examples of these substituents include halogen atoms such as, e.g., F, Cl, and Br.

The above aryl and aryloxy groups will often be phenyl and phenoxy groups. The aryl and aryloxy groups may be substituted with one or more (e.g., 1, 2, 3, 4, or 5) substituents. If more than one substituent is present, the substituents may be the same or different. Non-limiting examples of these substituents include nitro, cyano, halogen such as, e.g., F, Cl, and Br, optionally halogen-substituted alkyl having from 1 to about 6 carbon atoms, e.g., from 1 to about 4 carbon atoms (for example, methyl or ethyl) and optionally halogen-substituted alkoxy having from 1 to about 6 carbon atoms, e.g., from 1 to about 4 carbon atoms (for example, methoxy or ethoxy). Non-limiting specific examples of substituted aryl and aryloxy groups include but are not limited to, tolyl, xylyl, ethylphenyl, chlorophenyl, bromophenyl, tolyloxy, xylyloxy, ethylphenoxy, chlorophenoxy, and bromophenoxy.

The above aralkyl and aralkoxy groups will often be benzyl, phenethyl, benzyloxy, or phenethoxy groups. These groups may be substituted (preferably on the aryl ring, if at all) with one or more (e.g., 1, 2, 3, 4, or 5) substituents. If more than one substituent is present, the substituents may be the same or different. Non-limiting examples of these substituents include nitro, cyano, halogen such as, e.g., F, Cl, and Br, optionally halogen-substituted alkyl having from 1 to about 6 carbon atoms, e.g., from 1 to about 4 carbon atoms (for example, methyl, or ethyl) and optionally halogen-substituted alkoxy having from 1 to about 6 carbon atoms, e.g., from 1 to about 4 carbon atoms (for example, methoxy, or ethoxy).

The dicyanates of formula (I)/(Ia) may be prepared by methods which are well known to those of skill in the art. For example, the dicyanates may be prepared by reaction of a corresponding bisphenol with a cyanogen halide. The bisphenols can be prepared, for example, by condensation of phenols with ketones using methods well known in the art. Examples of these methods are described in, e.g., U.S. Pat. No. 4,438,241 and DE 3345945, the entire disclosures whereof are incorporated by reference herein. Generally speaking, the ketone is treated with a large excess of a phenol in the presence of an acid catalyst, non-limiting examples of which include mineral acids such as HCl or $H_2SO_4$, arylsulfonates, oxalic acid, formic acid, or acetic acid. A cocatalyst such as, e.g., a mercaptan may be added. Rather than using a soluble acid catalyst, it is also common to use a bed of sulfonated crosslinked polystyrene beads. Non-limiting examples of suitable ketone starting materials include cycloaliphatic ketones such as, e.g., cyclododecanone, cyclodecanone, adamantanone and other ketones derived from polycyclic hydrocarbons as well as aliphatic ketones such as, e.g., 2-octanone, 3-octanone, 2-nonanone, 3-nonanone, 2,4,8-trimethyl-4-nonanone, 2-decanone, 3-decanone, 2-undecanone, 6-undecanone, 2-methyl-4-undecanone, 2-dodecanone, 3-dodecanone and 4-dodecanone. Non-limiting examples of suitable phenol starting materials include phenol, o-cresol, m-cresol, p-cresol, o-chlorophenol, o-bromophenol, 2-ethylphenol, 2-octylphenol, 2-nonylphenol, 2,6-xylenol, 2-t-butyl-5-methylphenol, 2-t-butyl-4-methylphenol, 2,4-di(t-butyl)phenol, 2-t-butylphenol, 2-sec-butylphenol, 2-n-butylphenol, 2-cyclohexylphenol, 4-cyclohexylphenol, 2-cyclohexyl-5-methylphenol, α-decalone, and β-decalone.

It is well known in the art that this condensation chemistry can give a mixture of products such as o-alkylation of the phenol, oligomers derived from multiple alkylation of the phenol by the ketone, and acid-catalyzed rearrangement products. These impurities can either be removed or left in the material used as starting material for the cyanation reaction. In some regards these impurities can be beneficial, in that they lower the melting point of the final cyanated product. This can make it easier to prepare to formulate the cyanate by making it more soluble and reducing the tendency to crystallize. The presence of the oligomers tends to increase the viscosity of the cyanate and therefore its formulated products. This can be a beneficial or harmful property depending on the application.

By way of non-limiting example, the dicyanate compounds, such as 1,1-bis(4-cyanatophenyl)cyclododecane, may be prepared by reacting a cycloalkane bisphenol, such as 1,1-bis(4-hydroxyphenyl)cyclododecane, with an about stoichiometric quantity or a slight stoichiometric excess (up to about 20 percent excess) of a cyanogen halide per phenolic hydroxyl group in the presence of an about stoichiometric quantity or a slight stoichiometric excess (up to about 20 percent excess) of a base compound per phenolic hydroxyl group and in the presence of a suitable solvent. This reaction may schematically be represented as follows (for the case of 1,1-bis(4-cyanatophenyl)cyclododecane):

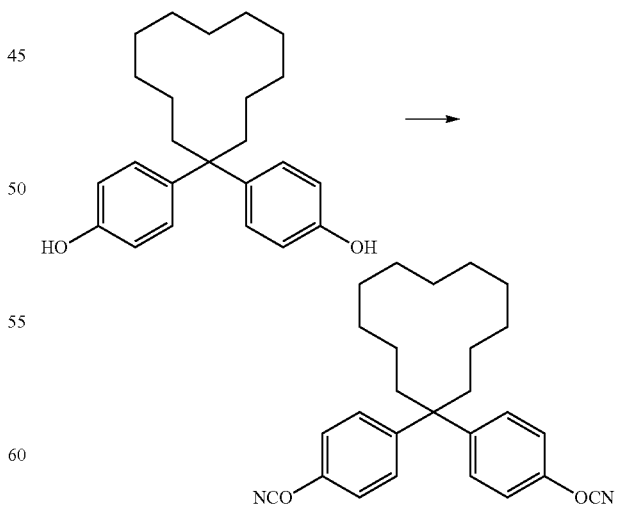

Usually reaction temperatures of from about −40° C. to about 60° C. are employed, with reaction temperatures of from about −15° C. to about 10° C. being preferred and reaction temperatures of from about −10° C. to about 0° C.

being particularly preferred. Reaction times can vary substantially, for example, as a function of the reactants being employed, the reaction temperature, solvent(s) used, the scale of the reaction, and the like, but are often in the range of from about 15 minutes to about 4 hours, with reaction times of from about 30 minutes to about 90 minutes being preferred.

Non-limiting examples of suitable cyanogen halides include cyanogen chloride and cyanogen bromide. Alternately, the method of Martin and Bauer described in Organic Synthesis, volume 61, pages 35-68 (1983), published by John Wiley and Sons, the entire disclosure of which is expressly incorporated by reference herein, can be used to generate the cyanogen halide in situ from sodium cyanide and a halogen such as chlorine or bromine.

Non-limiting examples of suitable base compounds for use in the above process include both inorganic bases and tertiary amines such as sodium hydroxide, potassium hydroxide, trimethylamine, triethylamine, and mixtures thereof. Triethylamine is most preferred as the base.

Non-limiting examples of suitable solvents for the cyanation reaction include water, aliphatic ketones, chlorinated hydrocarbons, aliphatic and cycloaliphatic ethers and diethers, aromatic hydrocarbons, and mixtures thereof. Acetone, methylethylketone, methylene chloride, and chloroform are particularly suitable as the solvent.

The aromatic dicyanate compounds of the present invention can usually be cured (thermoset) by heating at a temperature of from about 50° C. to about 400° C., preferably by heating at a temperature of from about 100° C. to about 250° C., optionally in the presence of a suitable catalyst.

Examples of suitable catalysts include acids, bases, salts, nitrogen and phosphorus compounds, such as for example, Lewis acids such as, e.g., $AlCl_3$, $BF_3$, $FeCl_3$, $TiCl_4$, $ZnCl_2$, and $SnCl_4$; protonic acids such as HCl, and $H_3PO_4$; aromatic hydroxy compounds such as phenol, p-nitrophenol, pyrocatechol, dihydroxynaphthalene; sodium hydroxide, sodium methylate, sodium phenolate, trimethylamine, triethylamine, tributylamine, diazabicyclo[2.2.2]octane, quinoline, isoquinoline, tetrahydroisoquinoline, tetraethylammonium chloride, pyridine-N-oxide, tributyl phosphine, zinc octoate, tin octoate, zinc naphthenate, cobalt naphthenate, cobalt octoate, cobalt acetylacetonate and the like. Also suitable as catalysts are metal chelates such as, for example, the chelates of transition metals and bidentate or tridentate ligands, particularly the chelates of iron, cobalt, zinc, copper, manganese, zirconium, titanium, vanadium, aluminum, and magnesium. These and other catalysts are disclosed in U.S. Pat. Nos. 3,694,410 and 4,094,852, the entire disclosures whereof are incorporated by reference herein. Cobalt naphthenate, cobalt octoate, and cobalt acetylacetonate are particularly suitable as the catalysts.

The quantity of catalyst(s) used, if any, may depend on the structure of the particular catalyst(s), the structure of the dicyanate compound being cured, the cure temperature, the cure time, and the like. Generally, catalyst concentrations of from about 0.001 to about 2 percent by weight, based on the total weight of the polymerizable components, are preferred.

B-staging or prepolymerization of the dicyanate compounds of the present invention can be accomplished by using lower temperatures and/or shorter curing times than those set forth above. Curing of a thus formed B-staged (prepolymerized) resin can then be accomplished at a later time or immediately following B-staging (prepolymerization) by increasing the temperature and/or the cure time.

The cured (thermoset) products prepared from the dicyanate compounds of the present invention comprise the cyanate group homopolymerization structure, i.e., the 1,3,5-triazine ring, unless other functionalities are present in the curable mixture that participate in the curing process and prevent a formation of the 1,3,5-triazine ring structure.

The aromatic dicyanate compounds of the present invention may be copolymerized with a variety of other compounds and/or prepolymers thereof. In corresponding copolymerizable mixtures, one or more dicyanates of formula (I)/(Ia) and/or prepolymers thereof may, for example, be present in quantities of from about 5% to about 95% by weight, e.g., from about 10% to about 90% by weight or from about 25% to about 75% by weight, based on the total weight of the polymerizable components.

Non-limiting examples of compounds (including prepolymers thereof) which may be copolymerized with the dicyanates of formula (I) and/or prepolymers thereof include compounds which comprise one or more polymerizable ethylenically unsaturated moieties, aromatic di- and polycyanates which are different from the dicyanates of formula (I), aromatic di- and polycyanamides, di- and polymaleimides, and di- and polyglycidyl ethers (epoxy resins) such as, e.g., diglycidyl ethers of bisphenol A or bisphenol F, polyglycidyl ethers of phenol novolac or cresol novolac resins and the epoxy resins disclosed in the co-assigned application entitled "POLYPHENOLIC COMPOUNDS AND EPOXY RESINS COMPRISING CYLCOALIPHATIC MOIETIES AND PROCESS FOR THE PRODUCTION THEREOF", filed concurrently herewith (U.S. application Ser. No. 12/921, 677), the entire disclosure whereof is expressly incorporated by reference herein.

Of course, it is also possible to copolymerize the aromatic dicyanate compounds of the present invention and/or prepolymers thereof with other components such as, e.g., one or more of (a) at least one compound which contains in the same molecule both a cyanate or cyanamide group and a polymerizable ethylenically unsaturated group; (b) at least one compound which contains in the same molecule both a 1,2-epoxide group and a polymerizable ethylenically unsaturated group; (c) at least one compound which contains in the same molecule both a maleimide group and a cyanate group; (d) at least one polyamine; and (e) at least one polyphenol, etc. Non-limiting specific examples of the use of dicyanates for making formulations which contain bismaleimides and epoxy resins and are useful for the production of high performance electrical laminates are disclosed in, e.g., U.S. Pat. No. 4,110,364, the entire disclosure whereof is incorporated herein by reference.

Specific and non-limiting examples of compounds (including prepolymers thereof) which may be copolymerized with the dicyanates of formula (I)/(Ia) include compounds of formula (III) and prepolymers thereof:

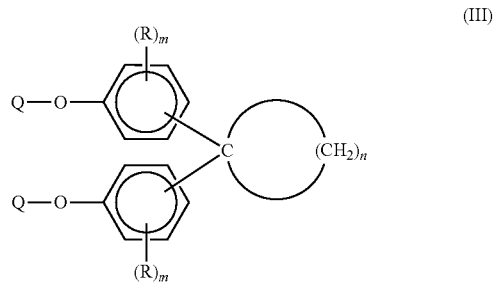

wherein:
n has a value of from about 5 to about 24;
each m independently is 0, 1, or 2;
the moieties R independently represent halogen, cyano, nitro, hydroxy, amino optionally carrying one or two alkyl groups preferably having from 1 to about 6 carbon atoms, unsubstituted or substituted alkyl preferably having from 1 to about 6 carbon atoms, unsubstituted or substituted cycloalkyl preferably having from about 5 to about 8 carbon atoms, unsubstituted or substituted alkoxy preferably having from 1 to about 6 carbon atoms, unsubstituted or substituted alkenyl preferably having from 3 to about 6 carbon atoms, unsubstituted or substituted alkenyloxy preferably having from 3 to about 6 carbon atoms, unsubstituted or substituted aryl preferably having from 6 to about 10 carbon atoms, unsubstituted or substituted aralkyl preferably having from 7 to about 12 carbon atoms, unsubstituted or substituted aryloxy preferably having from 6 to about 10 carbon atoms, and unsubstituted or substituted aralkoxy preferably having from 7 to about 12 carbon atoms; and
the moieties Q independently represent hydrogen, cyano, $HR^1C=CR^1—CH_2—$, or $H_2R^1C—CR^1=HC—$ wherein the moieties $R^1$ independently represent hydrogen or unsubstituted or substituted alkyl having from 1 to about 3 carbon atoms;
with the provisos that (1) when both moieties Q are hydrogen, at least one moiety R represents $HR^1C=CR^1—CH_2—$ or $H_2R^1C—CR^1=HC—$, (2) not more than one group Q represents cyano and (3) any non-aromatic cyclic moieties comprised in the above formula (III) may optionally carry one or more substituents and/or may optionally comprise one or more double bonds and/or may optionally be polycyclic (e.g., bicyclic or tricyclic).

Regarding the cycloaliphatic moiety shown in formula (III) and the meanings of n, m and R in formula (III) the comments set forth above with respect to the compounds of formula (I)/(Ia) apply in their totality.

The moieties Q in the above formula (III) independently represent hydrogen, cyano, $HR^1C=CR^1—CH_2—$ or $H_2R^1C—CR^1=HC—$ wherein the moieties $R^1$ independently represent hydrogen or unsubstituted or substituted (preferably unsubstituted) alkyl having from 1 to about 3 carbon atoms. A preferred moiety Q is allyl. Also, it is preferred for the moieties Q to be identical and to represent $HR^1C=CR^1—CH_2—$ or $H_2R^1C—CR^1=HC—$ and/or to be different from hydrogen. Also preferably, at least one of the moieties Q is not hydrogen.

Non-limiting specific examples of the above alkyl moieties $R^1$ include methyl, ethyl, propyl, and isopropyl. Methyl is preferred. If one or more substituents are present on these alkyl groups they may, for example, be halogen such as, e.g., F, Cl, and Br.

Non-limiting examples of the above compounds of formula (III) include 1,1-bis(4-hydroxyphenyl)cyclododecane bis(allyl ether), 1,1-bis(4-hydroxyphenyl)-cyclododecane bis(methallyl ether), 1,1-bis(4-hydroxyphenyl)-cyclododecane bis(1-propenyl ether), 1,1-bis(4-hydroxyphenyl)cyclodecane bis(allyl ether), 1,1-bis(4-hydroxyphenyl)cyclodecane bis(methallyl ether), 1,1-bis(4-hydroxyphenyl)-cyclodecane bis(1-propenyl ether), 2,2-bis(4-hydroxyphenyl)adamantane bis(allyl ether), 2,2-bis(4-hydroxyphenyl)adamantane bis(methallyl ether), 4,4'-bis(4-hydroxyphenyl)octahydro-1,4:5,8-dimethanonaphthalen-2(1H)ylidene bis(allyl ether), 4,4'-bis(4-hydroxyphenyl)octahydro-1,4:5,8-dimethanonaphthalen-2(1H)ylidene bis(methallyl ether), 5,5-bis(4-hydroxyphenyl)hexahydro-4,7-methanoindane bis(allyl ether) and 5,5-bis(4-hydroxyphenyl)hexahydro-4,7-methanoindane bis(methallyl ether).

Further non-limiting examples of the above compounds of formula (III) include partial or complete Claisen rearrangement products of compounds of formula (III) wherein at least one of the moieties Q represents $HR^1C=CR^1—CH_2—$ or $H_2R^1C—CR^1=HC—$, as well as monomers which carry at least one substituent on at least one aromatic ring to block a Claisen rearrangement.

The compounds of formula (III) may prepared by methods which are well known to those of skill in the art. For example, these monomers may be prepared by etherification of a cycloalkane bisphenol of the above formula (II) with a compound which comprises a group $HR^1C=CR^1—CH_2—$ or $H_2R^1C—CR^1=HC—$. In this regard, reference may also be made to the co-assigned application entitled "ETHYLENICALLY UNSATURATED MONOMERS COMPRISING ALIPHATIC AND AROMATIC MOIETIES", filed concurrently herewith (U.S. application Ser. No. 12/921,846), the entire disclosure of which is expressly incorporated by reference herein.

By way of non-limiting example, the allylation of a bisphenol of formula (II) may be accomplished via a transcarbonation reaction using, for example, allyl methyl carbonate, or a direct allylation reaction using, for example, an allyl halide, a methallyl halide and the like plus an alkaline agent and optional catalyst such as a phase transfer catalyst.

A direct allylation reaction of the bisphenol of the above formula (II) with an allyl halide such as allyl chloride may, for example, be conducted in the presence of an alkaline agent such as an aqueous solution of an alkali metal hydroxide (e.g., NaOH). If desired, inert solvents such as, e.g., 1,4-dioxane and phase transfer catalysts such as, e.g., benzyltrialkylammonium halides or tetraalkylammonium halides can be employed.

Further specific and non-limiting examples of compounds (including prepolymers thereof) which may be copolymerized with the aromatic dicyanates of formula (I)/(Ia) include compounds of formula (IV) and prepolymers thereof:

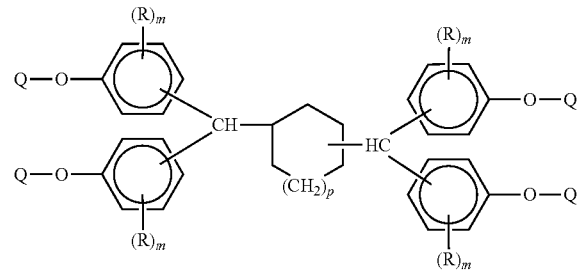

(IV)

wherein:
p is 0 or an integer of from 1 to about 19;
each m independently is 0, 1, or 2;
the moieties R independently represent halogen, cyano, nitro, unsubstituted or substituted alkyl preferably having from 1 to about 6 carbon atoms, unsubstituted or substituted alkoxy preferably having from 1 to about 6 carbon atoms, unsubstituted or substituted alkenyl preferably having from 3 to about 6 carbon atoms, unsubstituted or substituted alkenyloxy preferably having from 3 to about 6 carbon atoms, unsubstituted or substituted aryl preferably having from 6 to about 10 carbon atoms, unsubstituted or substituted aralkyl preferably having from 7 to about 12 carbon atoms, unsubstituted or substituted aryloxy preferably having from 6 to about 10 carbon atoms, and unsubstituted or substituted aralkoxy preferably having from 7 to about 12 carbon atoms; and
the moieties Q independently represent hydrogen, cyano, $HR^1C=CR^1-CH_2-$, or $H_2R^1C-CR^1=HC-$ wherein the moieties $R^1$ independently represent hydrogen or unsubstituted or substituted alkyl having from 1 to about 3 carbon atoms;
with the proviso that when all four moieties Q are hydrogen, at least one moiety R represents $HR^1C=CR^1-CH_2-$ or $H_2R^1C-CR^1=HC-$;
and any non-aromatic cyclic moieties comprised in the above formula (IV) may optionally carry one or more substituents and/or may optionally comprise one or more double bonds.

In the above formula (IV), p is 0 or an integer of from 1 to about 19, e.g., up to about 14, up to about 12 or up to about 8 such as, e.g., 1, 2, 3, 4, 5, 6, and 7, with 1, 2, or 3 being preferred and 1 being particularly preferred. Regarding exemplary and preferred meanings of n, R, Q and $R^1$ in formula (IV) the comments with respect to the above formulae (I) and (III) apply in their entirety and are expressly referred to.

Non-limiting specific examples of the above compounds of formula (IV) include (for $Q=HR^1C=CR^1-CH_2-$ or $H_2R^1C-CR^1=HC-$) dimethylcyclohexane tetraphenol tetra(allyl ether), dimethylcyclohexane tetraphenol tetra(methallyl ether), dimethylcyclohexane tetraphenol tetra(1-propenyl ether), dimethylcyclooctane tetraphenol tetra(allyl ether), dimethylcyclooctane tetraphenol tetra(methallyl ether), dimethylcyclooctane tetraphenol tetra(1-propenyl ether), partial or complete Claisen rearrangement products of dimethylcyclohexane tetraphenol tetra(allyl ether), and compounds which carry at least one substituent on at least one aromatic ring to block a Claisen rearrangement. Non-limiting specific examples of the above compounds of formula (IV) further include (for Q=—CN) dimethylcyclohexane tetraphenol tetracyanate, and dimethylcyclooctane tetraphenol tetracyanate.

The compounds of the above formula (IV) may be prepared, for example, by a process which comprises the condensation of a dialdehyde of a corresponding cycloalkane, which comprises from about 5 to about 24 ring carbon atoms, with a corresponding hydroxyaromatic (e.g., phenolic) compound (such as, e.g., phenol) at a molar ratio of aromatic hydroxy groups to aldehyde groups, which affords a mixture of polyphenolic compounds with a polydispersity (Mw/Mn) of not higher than about 2, e.g., not higher than about 1.8, or not higher than about 1.5, and optionally subjecting the mixture of polyphenolic compounds to an etherification reaction and/or cyanation reaction (e.g., with a cyanogen halide, see above) to partially or completely convert the phenolic groups which are present in the mixture into cyanate groups (—OCN) and/or into ether groups of formula $HR^1C=CR^1-CH_2-O-$ and/or $H_2R^1C-CR^1=HC-O-$ wherein the moieties $R^1$ independently represent hydrogen or unsubstituted or substituted alkyl having from 1 to about 3 carbon atoms. This process affords the compounds of formula (IV) in admixture with other monomers of similar structure but with higher (and lower) molecular weights (higher or lower degree of condensation).

The cycloaliphatic dialdehydes which are starting materials for the above process may be prepared by methods which are well known to those of skill in the art. By way of non-limiting example, cyclohexane dialdehyde can be produced by a hydroformylation of cyclohex-3-ene carboxaldehyde. This process produces a mixture of 1,3- and 1,4-cyclohexane dicarboxaldehydes. Condensation of this mixture of dialdehydes with phenol affords a novolac which comprises cyclohexane dialdehyde tetraphenol along with compounds with a higher and lower degree of condensation. The process renders it possible to produce very low polydispersity products with a high average functionality. For example, when using phenol and cyclohexane dialdehyde as starting materials, products having a weight average molecular weight (Mw) of about 930 and a number average molecular weight (Mn) of about 730 and/or an average of about 6 hydroxy groups per molecule can routinely be produced. The process preferably uses a relatively high molar ratio of aromatic hydroxy group to aldehyde group (e.g., about 6:1) to keep oligomerization low. The excess hydroxyaromatic compound may then be removed, for example, by distillation. In this regard, reference may also be made to the co-assigned application entitled "AROMATIC POLYCYANATE COMPOUNDS AND PROCESS FOR THE PRODUCTION THEREOF", filed concurrently herewith (Ser. No. 12/921,699), the entire disclosure of which is expressly incorporated by reference herein, as well as the above-mentioned co-assigned application entitled "POLYPHENOLIC COMPOUNDS AND EPOXY RESINS COMPRISING CYLCOALIPHATIC MOIETIES AND PROCESS FOR THE PRODUCTION THEREOF" (U.S. application Ser. No. 12/921,677).

By way of non-limiting example, the allylation of a cycloalkane tetraphenol such as, e.g., cyclohexane dialdehyde tetraphenol (and related phenolic compounds which may be present in admixture therewith) may be accomplished via a transcarbonation reaction using, for example, allyl methyl carbonate or a direct allylation reaction using, for example, an allyl halide, a methallyl halide, and the like plus an alkaline agent and an optional catalyst such as a phase transfer catalyst. In this regard, the corresponding further comments set forth above with respect to the allylation of compounds of formula (II) may be referred to.

The (co)polymerizable mixtures of the present invention and the products made therefrom respectively, may further comprise one or more other substances such as, e.g., one or more additives which are commonly present in polymerizable mixtures and products made therefrom. Non-limiting examples of such additives include polymerization catalysts, co-curing agents, flame retardants, synergists for flame retardants, solvents, fillers, glass fibers, adhesion promoters, wetting aids, dispersing aids, surface modifiers, thermoplastic resins, and mold release agents.

Non-limiting examples of co-curing agents for use in the present invention include dicyandiamide, substituted guanidines, phenolics, amino compounds, benzoxazine, anhydrides, amido amines, and polyamides.

Non-limiting examples of catalysts for use in the present invention (in addition to those set forth above with respect to the homopolymerization of the dicyanates of formula (I)) include transition metal complexes, imidazoles, phosphonium salts, phosphonium complexes, tertiary amines, hydrazides, "latent catalysts" such as Ancamine 2441 and K61B (modified aliphatic amines available from Air Products), Ajinomoto PN-23 or MY-24, and modified ureas.

Non-limiting examples of flame retardants and synergists for use in the present invention include phosphorus containing molecules (DOP—epoxy reaction product), adducts of DOPO (6H-dibenz[c,e][1,2]oxaphosphorin-6-oxide), magnesium hydrate, zinc borate and metallocenes.

Non-limiting examples of solvents for use in the present invention (for example, for improving processability) include acetone, methylethyl ketone, and Dowanol PMA (propylene glycol methyl ether acetate available from Dow Chemical Company).

Non-limiting examples of fillers for use in the present invention include functional and non-functional particulate fillers with a particle size range of from about 0.5 nm to about 100 μm. Specific examples thereof include silica, alumina trihydrate, aluminum oxide, metal oxides, carbon nanotubes, silver flake or powder, carbon black, and graphite.

Non-limiting examples of adhesion promoters for use in the present invention include modified organosilanes (epoxidized, methacryl, amino, allyl, etc.), acetylacetonates, sulfur containing molecules, titanates, and zirconates.

Non-limiting examples of wetting and dispersing aids for use in the present invention include modified organosilanes such as, e.g., Byk 900 series and W 9010, and modified fluorocarbons.

Non-limiting examples of surface modifiers for use in the present invention include slip and gloss additives, a number of which are available from Byk-Chemie, Germany.

Non-limiting examples of thermoplastic resins for use in the present invention include reactive and non-reactive thermoplastic resins such as, e.g., polyphenylsulfones, polysulfones, polyethersulfones, polyvinylidene fluoride, polyetherimides, polyphthalimides, polybenzimidazoles, acrylics, phenoxy resins, and polyurethanes.

Non-limiting examples of mold release agents for use in the present invention include waxes such as, e.g., carnauba wax.

The aromatic dicyanate compounds of the present invention are useful, inter alia, as thermosettable comonomers for the production of printed circuit boards and materials for integrated circuit packaging (such as IC substrates). They are especially useful for formulating matrix resins for high speed printed circuit boards, integrated circuit packaging, and underfill adhesives. As a comonomer, they may also be used to adjust the amount of hydrocarbon in a thermoset matrix.

Example 1

Synthesis of 1,1-Bis(4-cyanatophenyl)cyclododecane

A 250 milliliter, three neck, glass, round bottom reactor was charged with 1,1-bis(4-hydroxyphenyl)cyclododecane (17.63 grams, 0.10 hydroxyl equivalent) and acetone (125 milliliters, 7.09 milliliter per gram of bisphenol). The reactor was additionally equipped with a condenser (maintained at 0° C.), a thermometer, an overhead nitrogen inlet (1 LPM $N_2$ used), and magnetic stirring. Stirring commenced to give a solution at 21.5° C. Cyanogen bromide (11.12 grams, 0.105 mole, 1.05:1 cyanogen bromide:hydroxyl equivalent ratio) was added to the solution and immediately dissolved therein. A dry ice-acetone bath for cooling was placed under the reactor followed cooling and equilibration of the stirred solution at −5° C. Triethylamine (10.17 grams, 0.1005 mole, 1.005 triethylamine:hydroxyl equivalent ratio) was added using a syringe in aliquots that maintained the reaction temperature at −5 to 0° C. The total addition time for the triethylamine was 30 minutes. Addition of the initial aliquot of triethylamine induced haziness in the stirred solution with further additions inducing formation of a white slurry of triethylamine hydrobromide.

After 8 minutes of post-reaction at −5 to 0.5° C., high pressure liquid chromatographic (HPLC) analysis of a sample of the reaction product revealed the presence of 0.68 area percent unreacted 1,1-bis(4-hydroxyphenyl)cyclododecane, 4.43 area % monocyanate, and 93.98 area % dicyanate, with the balance as 7 minor peaks. After a cumulative 45 minutes of postreaction at −5° C. to 0° C., HPLC analysis of a sample of the reaction product revealed the presence of 0.84 area percent unreacted cyclododecane bisphenol, 5.34 area % monocyanate, and 93.51 area % dicyanate, with the balance as one minor peak.

After a cumulative 101 minutes of post-reaction, the product slurry was added to a beaker of magnetically stirred deionized water (1.5 liters) providing an aqueous slurry. After 5 minutes of stirring, gravity filtration of the aqueous slurry through filter paper recovered the white powder product. The product from the filter paper was rinsed into a beaker using deionized water to a total volume of 200 milliliters, followed by the addition of dichloromethane (200 milliliters). A solution formed in the dichloromethane layer. The mixture was added to a separatory funnel, thoroughly mixed, allowed to settle, and then the dichloromethane layer recovered, with the aqueous layer discarded to waste. The dichloromethane solution was added back into the separatory funnel and extracted with fresh deionized water (200 milliliters) two additional times.

The resultant hazy dichloromethane solution was dried over granular anhydrous sodium sulfate (5 grams) to give a clear solution which was then passed through a bed of anhydrous sodium sulfate (25 grams) supported on a 60 milliliter, medium fritted glass funnel attached to a side arm vacuum flask. The clear filtrate was rotary evaporated using a maximum oil bath temperature of 50° C. until the vacuum was <3.5 mm Hg. A total of 19.81 grams (98.43% uncorrected, isolated yield) of white, crystalline product was recovered. HPLC analysis of a sample of the product revealed the presence of 0.47 area percent unreacted 1,1-bis(4-hydroxyphenyl)cyclododecane, 3.09 area % monocyanate, and 96.44 area % dicyanate.

Example 2

Synthesis of the Homopolytriazine of the 1,1-Bis(4-cyanatophenyl)cyclododecane

Differential scanning calorimetry (DSC) analysis of a portion (9.8 milligrams) of 1,1-bis(4-cyanatophenyl)cyclododecane from Example 1 above was completed using a rate of heating of 7° C. per minute from 25° C. to 400° C. under a stream of nitrogen flowing at 35 cubic centimeters per minute. A single melt endotherm was detected with a 120.8° C. onset, a 129.6° C. midpoint, and a 136.0° C. end, accompanied by an enthalpy of 4.5 joules per gram. A single exotherm attributed to cyclotrimerization was detected with a 194.8° C. onset, a 289.4° C. midpoint, and a 340.3° C. end, accompanied by an enthalpy of 562.3 joules per gram. A second scanning of the resultant homopolytriazine revealed a weak transition at 202.1° C. which may be a glass transition temperature. The homopolytriazine recovered from the DSC analysis was a transparent, light amber colored, rigid solid.

Example 3

Synthesis and Recrystallization to Produce High Purity 1,1-Bis(4-cyanatophenyl)cyclododecane The synthesis of 1,1-bis(4-cyanatophenyl)cyclododecane of Example 1 was repeated, but with a 2-fold increase in scale. The 38.86 grams of recovered product assayed 0.69 area percent unreacted 1,1-bis(4-hydroxyphenyl)cyclododecane, 3.91 area % monocyanate, and 95.40 area % dicyanate by HPLC analysis. Recrystallization was performed by forming a solution in boiling acetone (50 milliliters), then holding for 24 hours at 23° C. The acetone solution was removed from the crystalline product via decantation. HPLC analysis of a portion of the damp crystalline product revealed the presence of no detectable unreacted 1,1-bis(4-hydroxyphenyl)cyclododecane, 1.02 area % monocyanate, and 98.98 area % dicyanate. A second recrystallization of the damp crystalline product from acetone (40 milliliters) followed by drying in the vacuum oven at 50° C. for 48 hours provided 20.12 grams of brilliant white product with no detectable unreacted 1,1-bis(4-hydroxyphenyl)cyclododecane, 0.42 area % monocyanate, and 99.58 area % dicyanate by HPLC analysis. Combination of the acetone solution decants from the two recrystallizations followed by concentration of the solution to a volume of 28 milliliters yielded a second crop of brilliant white product (8.39 grams) with a trace (non-integratable) of unreacted 1,1-bis(4-hydroxyphenyl)cyclododecane, 2.28 area % monocyanate, and 97.72 area % dicyanate by HPLC analysis.

Reference Example 1

Synthesis of the Bis(Allyl Ether) of 1,1-Bis(4-hydroxyphenyl)cyclododecane

Allyl alcohol (101.58 grams, 1.75 moles), dimethyl carbonate (157.55 grams, 1.75 moles), and sodium methoxide catalyst (0.18 gram, 0.065 percent by weight) were added to a 500 milliliter, 3 neck, round bottom glass reactor and maintained at room temperature (23° C.) with stirring under a nitrogen atmosphere. The reactor was additionally outfitted with a chilled condenser, a thermometer, magnetic stirring, and a thermostatically controlled heating mantle. An equilibrium mixture of allylmethyl carbonate, diallyl carbonate, and methanol was rapidly formed concurrent with cooling of the reactor contents to 15.5° C. After 13 minutes 1,1-bis(4-hydroxyphenyl)cyclododecane (28.31 grams, 0.1606 equivalent of hydroxy groups), was added to the reactor followed by a mixture of triphenylphosphine (0.56 gram, 0.204 percent by weight) and 5% palladium on carbon (0.38 gram, 0.127 percent by weight). The 1,1-bis(4-hydroxyphenyl)cyclododecane assayed 99.76 area % via high pressure liquid chromatographic (HPLC) analysis with the balance consisting of 2 minor components (0.09 and 0.15 area %). Heating commenced and over the next 127 minutes the reaction temperature reached 79-80° C. The reaction mixture was maintained for 8 hours at 77.5-80° C. and then cooled to room temperature and vacuum filtered through a bed of diatomaceous earth packed on a medium fritted glass funnel. The recovered filtrate was rotary evaporated at a maximum oil bath temperature of 100° C. and to a vacuum of 1.7 mm Hg pressure to provide a transparent, light yellow colored, liquid (35.04 grams) which became a tacky solid at room temperature.

HPLC analysis revealed the presence of 96.78 area % allyl ether of 1,1-bis(4-hydroxyphenyl)cyclododecane with the balance as a single minor component (3.22 area %). The single minor component was removed by dissolving the product in dichloromethane (100 milliliters) and passing the resultant solution through a 2 inch deep by 1.75 inch diameter bed of silica gel (230-400 mesh particle size, 60 angstrom mean pore size, 550 $m^2$/gram surface dimension) supported on a medium fritted glass funnel. After elution from the silica gel bed with additional dichloromethane, a yellow band remained in the region of the origin. Rotary evaporation provided 33.98 grams (98.94% isolated yield) of pale yellow colored tacky solid.

HPLC analysis revealed the presence of 99.57 area % allyl ether of 1,1-bis(4-hydroxyphenyl)cyclododecane with the balance as 2 minor components (0.22 and 0.21 area %). Infrared spectrophotometric analysis of a film sample of the product on a KBr plate revealed peaks in the range expected for unsaturated C—H stretch (3032, 3058, 3081 $cm^{-1}$), saturated C—H stretch (2862, 2934 $cm^{-1}$ [shoulder present on both]), C=C stretch (1581, 1607 $cm^{-1}$), C—O stretch (1026 $cm^{-1}$), and CH=$CH_2$ deformation (924, 998 $cm^{-1}$), accompanied by total absence of hydroxyl group absorbance thus confirming full conversion of the phenolic hydroxyl groups to allyl ether groups.

Example 4

Thermally Induced Copolymerization of Bis(Allyl Ether) of 1,1-Bis(4-hydroxyphenyl)cyclododecane (25% wt.) and 1,1-Bis(4-cyanatophenyl)cyclododecane (75% wt.)

1,1-Bis(4-cyanatophenyl)cyclododecane (0.5034 gram, 75% wt.) and bis(allyl ether) of 1,1-bis(4-hydroxyphenyl) cyclododecane (0.1678 gram, 25% wt.) from Reference Example 1 were weighed into a glass vial to which dichloromethane (1.5 milliliters) was added. HPLC analysis of the 1,1-bis(4-cyanatophenyl)cyclododecane revealed 99.44 area % dicyanate, and 0.56 area % monocyanate. Shaking the vial provided a solution which was added to an aluminum tray. Devolatilization conducted in a vacuum oven at 40° C. for 30 minutes removed the dichloromethane, giving a homogeneous blend. DSC analysis of portions (9.70 and 10.00 milligrams) of the blend was conducted using a rate of heating of 5° C. per minute from 25° C. to 400° C. under a stream of nitrogen flowing at 35 cubic centimeters per minute.

An endotherm was observed with an average 99.0° C. onset (98.07 and 99.96° C.), 118.8° C. minimum (118.72 and 118.93° C.), and 126.5° C. endpoint (124.61 and 128.40° C.), accompanied by an enthalpy of 11.5 joules per gram (10.13 and 12.76 joules per gram) (individual values in parenthesis). An exotherm attributed to copolymerization of the allyl and cyanate groups (plus any homopolymerization) was observed with an average 172.2° C. onset (170.58° C. and 173.90° C.), 249.1° C. maximum (248.30° C. and 249.80° C.), and 292.9° C. endpoint (289.54° C. and 296.18° C.) accompanied by an enthalpy of 487.1 joules per gram (474.9 and 499.2 joules per gram) (individual values in parenthesis). The copolymer recovered from the DSC analysis was a transparent, amber colored, rigid solid.

Example 5

Glass Transition Temperature of Copolymer of Bis(Allyl Ether) of 1,1-Bis(4-hydroxyphenyl)cyclododecane (25% wt.) and Dicyanate of Cyclododecane Bisphenol (75% wt.)

Curing of the remaining blend from Example 4 was completed in an oven using the following curing schedule: 150° C. for 1 hour, 200° C. for 1 hour, 250° C. for 1 hour. DSC analysis of portions (28.2 and 35.0 milligrams) of the cured product gave an average glass transition temperature of 214.3° C. (212.85° C. and 215.83° C.) (individual values in parenthesis).

Example 6

Thermally Induced Copolymerization of Bis(Allyl Ether) of 1,1-Bis(4-hydroxyphenyl)cyclododecane (50% wt.) and 1,1-Bis(4-cyanatophenyl)cyclododecane (50% wt.)

1,1-Bis(4-cyanatophenyl)cyclododecane (0.2978 gram, 50% wt.) and bis(allyl ether) of 1,1-bis(4-hydroxyphenyl)cyclododecane (0.2978 gram, 50% wt.) from Reference Example 1 were weighed into a glass vial to which dichloromethane (1.5 milliliters) was added. HPLC analysis of the 1,1-bis(4-cyanatophenyl)cyclododecane revealed 99.44 area % dicyanate and 0.56 area % monocyanate. Shaking the vial provided a solution which was added to an aluminum tray. Devolatilization conducted in a vacuum oven at 40° C. for 30 minutes removed the dichloromethane, giving a homogeneous blend.

DSC analysis of portions (9.70 and 10.70 milligrams) of the blend was conducted using a rate of heating of 5° C. per minute from 25° C. to 400° C. under a stream of nitrogen flowing at 35 cubic centimeters per minute. No endotherm was observed. An exotherm attributed to copolymerization of the allyl and cyanate groups (plus any homopolymerization) was observed with an average 173.7° C. onset (171.05° C. and 176.27° C.), 246.5° C. maximum (245.96° C. and 247.01° C.), and 282.0° C. endpoint (281.01° C. and 282.91° C.), accompanied by an enthalpy of 414.2 joules per gram (403.2 and 425.1 joules per gram) (individual values in parenthesis). The copolymer recovered from the DSC analysis was a transparent, amber colored, rigid solid.

Example 7

Glass Transition Temperature of Copolymer of Bis (Allyl Ether) of 1,1-Bis(4-hydroxyphenyl)cyclododecane (50% wt.) and 1,1-Bis(4-cyanatophenyl)cyclododecane (50% wt.)

Curing of the remaining blend from Example 6 was conducted in an oven using the following curing schedule: 150° C. for 1 hour, 200° C. for 1 hour, 250° C. for 1 hour. DSC analysis of portions (33.8 and 34.3 milligrams) of the cured product gave residual exothermicity at >260° C. After a second scanning an average glass transition temperature of 144.57° C. (140.98° C. and 148.15° C.) (individual values in parenthesis) was measured. A third scanning was completed since residual exothermicity was observed at >330° C. An average glass transition temperature of 160.03° C. (159.52° C. and 160.53° C.) with no residual exothermicity observed.

Example 8

Copolymerization of Bis(Allyl Ether) of 1,1-Bis(4-hydroxyphenyl)cyclododecane (25% wt.) and 1,1-Bis(4-cyanatophenyl)cyclododecane (75% wt.) Using Catalyst 1,1-Bis(4-cyanatophenyl)cyclododecane (0.7709 gram, 75% wt.), bis(allyl ether) of 1,1-bis(4-hydroxyphenyl)cyclododecane (0.2570 gram, 25% wt.) from Reference Example 1, and 6% cobalt naphthenate (0.0051 gram, 0.5% wt.) were weighed into a glass vial to which dichloromethane (1.5 milliliters) was added. HPLC analysis of the 1,1-bis(4-cyanatophenyl)cyclododecane revealed 99.44 area % dicyanate and 0.56 area % monocyanate. Shaking the vial provided a solution which was added to an aluminum tray. Devolatilization conducted in a vented oven at 40° C. for 30 minutes removed the dichloromethane, giving a homogeneous blend.

DSC analysis of portions (10.1 and 12.5 milligrams) of the blend was conducted using a rate of heating of 5° C. per minute from 25° C. to 400° C. under a stream of nitrogen flowing at 35 cubic centimeters per minute. An endotherm was observed with an average 51.62° C. onset (41.67° C. and 61.57° C.), 85.29° C. minimum (79.93° C. and 90.64° C.), and 93.09° C. endpoint (90.48° C. and 95.70° C.) accompanied by an enthalpy of 16.22 joules per gram (8.65 and 23.79 joules per gram) (individual values in parenthesis). An exotherm attributed to a copolymerization of the allyl and cyanate groups (plus any homopolymerization) was observed with an average 93.09° C. onset (90.48° C. and 95.70° C.), 162.04° C. and 238.36° C. maxima that merged together (161.28° C., 162.79° C., 236.93° C., and 239.78° C.), and 283.38° C. endpoint (282.43° C. and 284.33° C.) accompanied by an enthalpy of 422.6 joules per gram (413.0 and 432.1 joules per gram) (individual values in parenthesis). The copolymer recovered from the DSC analysis was a transparent, amber colored, rigid solid.

Example 9

Thermogravimetric Analysis (TGA) and Differential Scanning Calorimetry (DSC) of Copolymer of Bis (Allyl Ether) of 1,1-Bis(4-hydroxyphenyl)cyclododecane (25% wt.) and 1,1-Bis(4-cyanatophenyl)cyclododecane (75% wt.) Prepared Using Catalyst 1,1-Bis(4-cyanatophenyl)cyclododecane (3.00 grams, 75% wt.), bis(allyl ether) of 1,1-bis(4-hydroxyphenyl)cyclododecane (1.00 gram, 25% wt.) from Reference Example 1, and 6% cobalt naphthenate (0.0040 gram, 0.1% wt.) were weighed into a glass vial to which dichloromethane (2.0 milliliters) was added. HPLC analysis of the dicyanate of cyclododecane bisphenol revealed 99.44 area % dicyanate and 0.56 area % monocyanate. Shaking the vial provided a solution which was added to a round aluminum pan. Devolatilization conducted in a vacuum oven at 50° C. for 30 minutes removed the dichloromethane giving a homogeneous blend. Curing was conducted in ovens using the following curing schedule: 100° C. for 1 hour, 150° C. for 1 hour, 200° C. for 2 hours, 250° C. for 1 hour. A rigid, transparent, amber colored disk was recovered after curing and demolding from the aluminum pan.

DSC analysis of portions (33.0 and 34.3 milligrams) of the cured product was conducted using a rate of heating of 5° C. per minute from 25° C. to 400° C. under a stream of nitrogen flowing at 35 cubic centimeters per minute. Residual exothermicity was observed at >260° C. and an average glass transition temperature of 181.83° C. (185.80° C. and 177.85° C.) (individual values in parenthesis) was measured. TGA of a portion (20.3110 milligrams) of the cured product was conducted using a rate of heating of 10° C. per minute from 25° C. to 600° C. under a dynamic nitrogen atmosphere. A step transition with an onset temperature of 400.42° C. and an end temperature of 446.57° C. was observed. The temperatures at 99.00, 95.00 and 90.00% of original sample weight were 243.23° C., 373.76° C. and 396.76° C., respectively.

Example 10

Moisture Resistance of Copolymer of Bis(Allyl Ether) of 1,1-Bis(4-hydroxyphenyl)cyclododecane (25% wt.) and 1,1-Bis(4-cyanatophenyl)cyclododecane (75% wt.) Prepared Using Catalyst The remaining portion of the cured copolymer disk from Example 9 was weighed, added to a 4 ounce glass jar along with deionized water (40 milliliters), sealed and then placed in an oven maintained at 55° C. The disk was removed at the indicated intervals, blotted dry, weighed, and then replaced back into the sealed jar for continuation of the testing. The change in weight from the original was calculated for each time interval, providing the following results given in the table.

| Exposure to Deionized Water at 55° C. | |
|---|---|
| Duration of Exposure (hours) | Copolymer of Example 10 (% wt. increase) |
| 9.0 | 0.573 |
| 25.33 | 0.768 |
| 51.83 | 0.859 |
| 95.16 | 1.055 |
| 119.08 | 1.081 |
| 143.00 | 1.068 |
| 167.17 | 1.081 |

Reference Example 2

Synthesis and Characterization of the Tetraphenol of Dimethylcyclohexane

Phenol (598 g, 6.36 moles) and cyclohexane dicarboxaldehyde (74.2 g, 0.53 moles, mixture of 1,3- and 1,4-isomers; ratio of phenolic groups to aldehyde groups=6:1, equivalent ratio of phenol to cyclohexane dicarboxaldehyde=3:1) were added together in a 1-L 5-neck reactor. The mixture was heated to 50° C. with 500 rpm mechanical stirrer agitation. At 50° C. and atmospheric pressure, p-toluenesulfonic acid (PTSA) (1.3959 g total, 0.207% by weight) was added in six portions over 30 minutes. The temperature increased a few degrees with each PTSA addition. After the 6th PTSA addition, the temperature controller was set to 70° C. and vacuum was applied to the reactor. In order to avoid the reactor content flooding the rectifier, the reactor pressure was gradually decreased to remove water from the reaction solution. When the reflux had stopped, the reactor was vented and water (48 g) was added.

Water (79 g) and NaHCO$_3$ (0.6212 g) were added to neutralize the PTSA. When the reaction contents had cooled to room temperature, the entire contents were transferred to a 2-L separatory funnel. Methyl ethyl ketone (MEK) was added, and the contents were washed several times with water to remove PTSA-salt. The solvents and excess phenol were removed using a rotary evaporator, and the hot novolac was poured onto aluminum foil. The reaction of phenol with cyclohexane dicarboxaldehyde produced as the predominant product a tetraphenol possessing the following idealized structure (tetraphenol of dimethylcyclohexane):

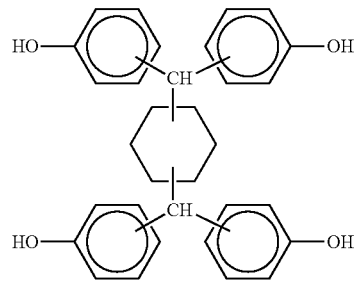

Ultraviolet spectrophotometric analysis provided a hydroxyl equivalent weight (HEW) of 118.64. High pressure liquid chromatographic (HPLC) analysis was adjusted to resolve 24 (isomeric) components present in the product.

Although the present invention has been described in considerable detail with regard to certain versions thereof, other versions are possible, and alterations, permutations, and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

What is claimed is:

1. A polymer or prepolymer of a dicyanate compound of formula (Ia):

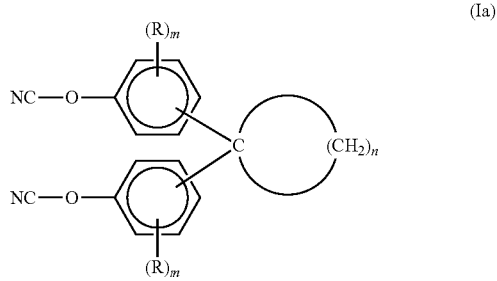

(Ia)

wherein:
each m independently is 1 or 2;
the moieties R independently represent halogen, cyano, nitro, optionally substituted alkyl, optionally substituted cycloalkyl, optionally substituted alkoxy, optionally substituted alkenyl, optionally substituted alkenyloxy, optionally substituted aryl having from 6 to about 10 carbon atoms, optionally substituted aralkyl having from 7 to about 12 carbon atoms, optionally substituted aryloxy having from 6 to about 10 carbon atoms, and optionally substituted aralkoxy having from 7 to about 12 carbon atoms and n has a value of from about 7 to about 24;

and any non-aromatic cyclic moieties comprised in the above formula (Ia) may optionally carry one or more substituents and/or may optionally comprise one or more double bonds and/or may optionally be polycyclic.

2. A polymerizable mixture, wherein the mixture comprises at least one dicyanate compound of claim 1 and/or a prepolymer thereof, and one or more substances which are selected from polymerization catalysts, co-curing agents, flame retardants, synergists for flame retardants, solvents, fillers, glass fibers, adhesion promoters, wetting aids, dispersing aids, surface modifiers, thermoplastic polymers, and mold release agents.

3. A polymerizable mixture, wherein the mixture comprises at least one (i) dicyanate compound of claim 1 and/or a prepolymer thereof and (ii) at least one compound and/or a prepolymer thereof which is capable of reacting with (i).

4. The mixture of claim 3, wherein the at least one compound (ii) is selected from compounds which comprise one or more polymerizable ethylenically unsaturated moieties, aromatic di- and polycyanates which are different from a dicyanate compound of formula (Ia), aromatic di- and polycyanamides, di- and polymaleimides, and di- and polyglycidyl ethers.

5. The mixture of claim 3, wherein the mixture further comprises one or more substances which are selected from polymerization catalysts, co-curing agents, flame retardants, synergists for flame retardants, solvents, fillers, glass fibers, adhesion promoters, wetting aids, dispersing aids, surface modifiers, thermoplastic polymers, and mold release agents.

6. The mixture of claim 2, wherein the mixture is partially or completely polymerized.

7. A product which comprises a polymerized mixture of claim 2.

8. The product of claim 7, wherein the product is at least one of an electrical laminate, an IC substrate, a casting, a coating, a die attach and mold compound formulation, a composite, and an adhesive.

9. A process for preparing the dicyanate compound of claim 1, wherein the process comprises reacting a compound of formula (II):

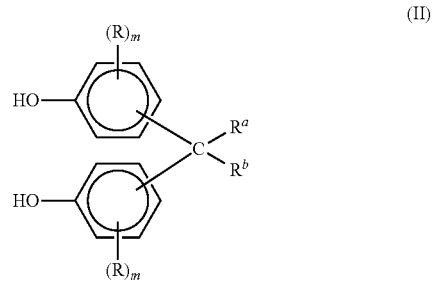

wherein m, $R^a$, $R^b$ and R are as set forth in claim 1 in a solvent with an at least about stoichiometric quantity of a cyanogen halide in the presence of an at least about stoichiometric quantity of a base.

10. The process of claim 9, wherein the cyanogen halide comprises at least one of cyanogen chloride and cyanogen bromide.

11. The process of claim 9, wherein the reaction is carried out at a temperature of from about −40° C. to about 60° C.

12. The process of claim 9, wherein the base comprises one or more of sodium hydroxide, potassium hydroxide, trimethylamine, and triethylamine.

13. The process of claim 9, wherein the base comprises triethylamine.

14. The process of claim 9, wherein the solvent comprises one or more of water, an aliphatic ketone, a chlorinated hydrocarbon, an aliphatic or cycloaliphatic ether or diether, and an aromatic hydrocarbon.

15. The process of claim 9, wherein the solvent comprises one or more of acetone, methylethylketone, methylene chloride, and chloroform.

* * * * *